United States Patent [19]

Lawrence et al.

[11] 4,121,586

[45] Oct. 24, 1978

[54] BLOW GUN INNOCULATING DART

[76] Inventors: Edward M. Lawrence; Brian E. Lawrence, both of 5146 NE. 78th Ave., Bondurant, Iowa 50035

[21] Appl. No.: 792,889

[22] Filed: May 2, 1977

[51] Int. Cl.[2] .......... A61M 5/00

[52] U.S. Cl. .......... 128/215; 128/DIG. 11; 273/106.5 D

[58] Field of Search .......... 128/215, DIG. 11, 218 R; 273/106.5 R, 106.5 D

[56] References Cited

U.S. PATENT DOCUMENTS

| | | | |
|---|---|---|---|
| 2,348,337 | 5/1944 | Francis | 128/DIG. 11 |
| 2,995,373 | 8/1961 | Cox | 128/DIG. 11 |
| 3,006,649 | 10/1961 | Gesick et al. | 273/106.5 D |

*Primary Examiner*—John D. Yasko

*Attorney, Agent, or Firm*—Zarley, McKee, Thomte, Voorhees & Sease

[57] ABSTRACT

An innoculating dart especially designed for use with blow guns. The dart can be accurately fired for distances up to in excess of 25 feet in order to innoculate and/or tranquilize animals. The dart is designed to expel its contained innoculating fluid, after being shot from a blow gun, upon impact with the target animal.

6 Claims, 8 Drawing Figures

BLOW GUN INNOCULATING DART

BACKGROUND OF THE INVENTION

In many instances, there exists a need for innoculating or tranquilizing either wild or domestic animals. For example, veterinarians often must innoculate and/or tranquilize domestic livestock. Additionally, it is very common for police officers, conservation officers, research biologists and zoo keepers, just to name a few, to have a need for innoculating animals in order to tranquilize them.

There exists now on the marketplace a variety of tranquilizing guns which can be used for such innoculations. However, tranquilizing guns have a particular disadvantage in urban areas, crowded park areas, or other such areas where dart guns having long range capabilities are not practical for use because of the inherent danger and noise.

Accordingly, this invention has as one of its objects the development of an innoculating dart which is specifically designed for use with a blow gun. The dart can be conveniently and silently expelled from the blow gun with a minimum of danger.

Another object of this invention is to provide a blow gun innoculating dart which has a high degree of accuracy for distances often up to as far as 40 feet.

Yet another object of this invention is to provide an innoculating dart which is of simple mechanical construction, can be easily prepared, and which expels its volume of innoculating agent automatically upon impact with an animal.

A still further object of this invention is to provide an innoculating dart especially designed for use with a blow gun which relies upon an easy break-away shear pin for quick and convenient innoculation upon impact with an animal.

A still further object of this invention is to design an innoculating dart which can utilize as an impact shear pin, a fine clay base mechanical pencil lead.

Another object of this invention is to provide an innoculating dart which can be quickly, conveniently and inexpensively made from a conventional medical hypodermic syringe with only a few minor modifications of such a syringe.

The method of accomplishing each of the above objects, as well as others, will become apparent from the following detailed description of the invention.

SUMMARY OF THE INVENTION

This invention pertains to an innoculating dart especially designed for blow guns which comprises a hollow syringe barrel, a tubular needle in communication with the interior portion of the syringe barrel, a plunger reciprocally mounted within the rearward end of the syringe barrel, a power head sealing pin mounted at the back of the plunger designed to fit in sealing relationship in the barrel of a blow gun, biasing means associated with the plunger to normally urge the plunger into a fluid released forward position, and a plurality of spaced apart transverse openings extending through the plunger so that an easy break-away shear pin may be extended through any one of the openings and at least partially across the rearward end of the syringe barrel to releasably hold the plunger in a cocked rearward position, with the barrel filled with fluid ready to release upon break-away of the shear pin and forward movement of the plunger, upon impact with an animal.

DETAILED DESCRIPTION OF THE INVENTION

Figure 1:
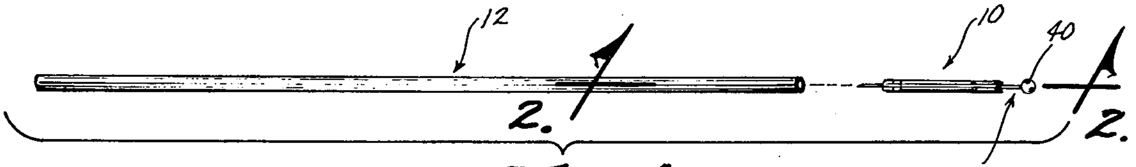
FIG. 1 is a perspective view showing the innoculating dart of this invention and a blow gun.
Figure 2:
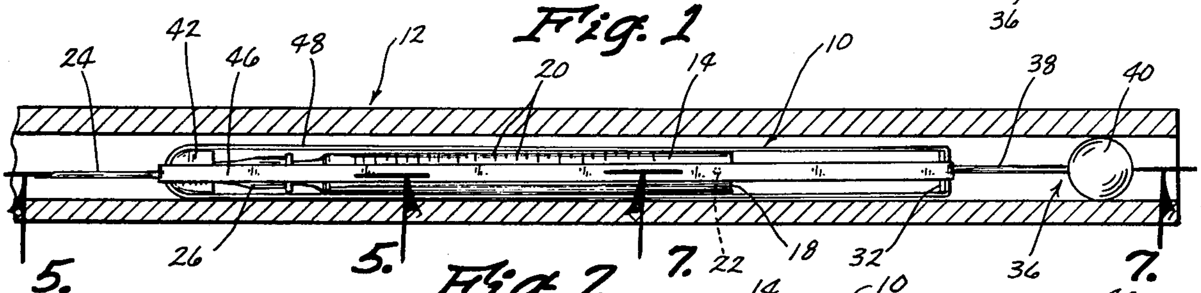
FIG. 2 is a view along line 2—2 of FIG. 1 showing the innoculating dart of this invention positioned within a blow gun ready for firing.
Figure 3:
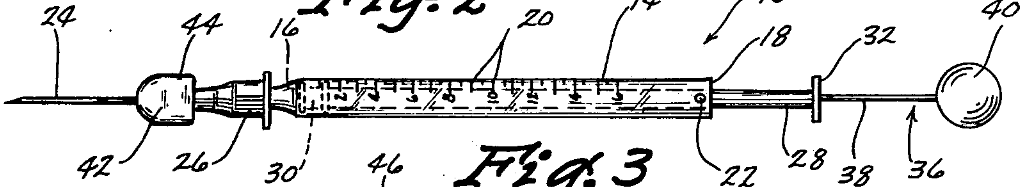
FIG. 3 is a plan view of the innoculating dart of this invention.
Figure 4:
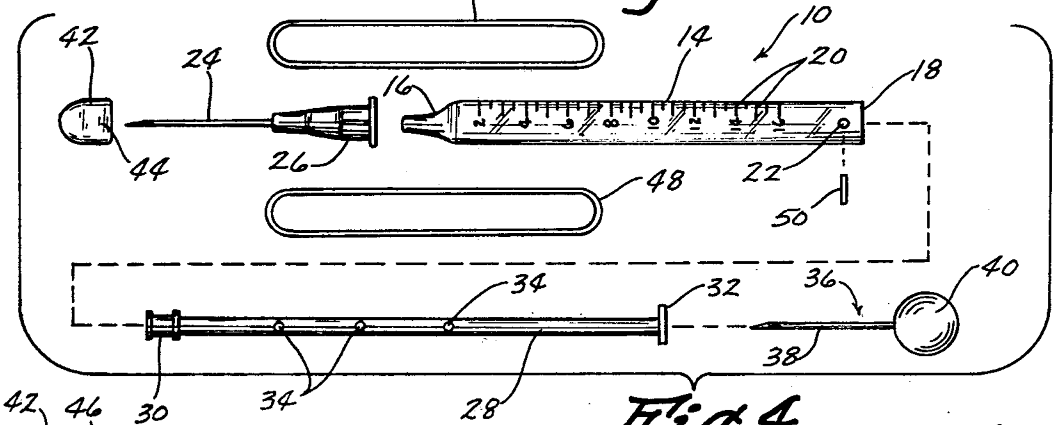
FIG. 4 shows the dart of this invention in disassembled condition.

The innoculating dart 10 is designed for use in a blow gun 12 of conventional construction. The dart 10 is comprised of a hollow syringe barrel 14 having a forward tapered end 16 and a rearward end 18. As can be depicted in the FIGS. 3 and 4, syringe barrel 14 has incremental measuring marks 20 visibly marked on its outside wall. Near the rearward end of syringe barrel 14 is alignment aperture 22, whose purpose will be described later.

Tubular needle 24 is in communication with the interior compartment of syringe barrel 14 and is positioned on the forward tapered end 16 of syringe barrel 14 via a conventional rubber or plastic sealer 26.

A plunger 28 is telescopically and reciprocally mounted within syringe barrel 14. Plunger 28 has a sealing gasket 30 at its forward end and a head 32 at its rearward end. At spaced apart intervals, intermediate forward and rearward ends of plunger 28 are a plurality of transversely extending openings 34.

A power head sealing pin 36 is comprised of a pin portion 38 and a sealing head 40. Sealing head 40 is preferably a plastic bead, and it has a diameter equal to the inside diameter of blow gun 12. Power head sealing pin 36 is inserted into plunger head 32 via pin portion 38.

The innoculating dart 10 is preferably provided with counterweight 42 which has a central opening so that it may be inserted over tubular needle 24 as depicted. Counterweight 42 preferably has flat side portions 44 in order to securely hold rubber bands 46 and 48 in position. Counterweight 42 has been found preferable in order to provide increased shooting distance and accuracy. There are, however, times when the syringe barrel 14 is of unusually large diameter such that the bulk weight of the innoculating fluid is so great that a counterweight 42 is not needed in order to provide the accurate longer range shooting. However, on most occasions, it is preferable to use a counterweight 42.

Figure 6:
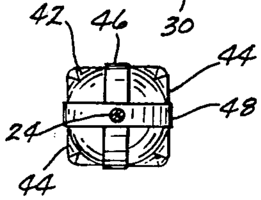
FIG. 6 is a view of the forward end of the dart along line 6—6 of FIG. 5.
Figure 5:
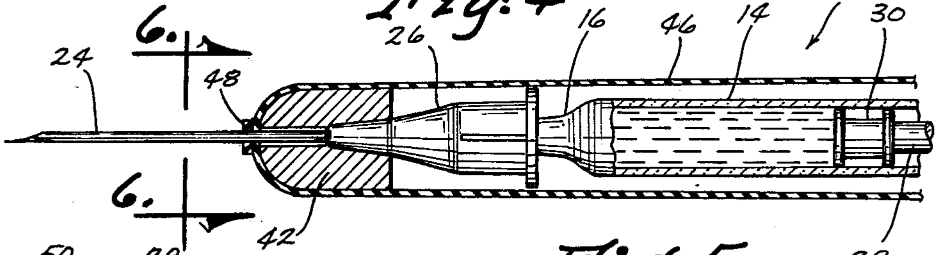
FIG. 5 is a sectional view, with certain parts broken away, showing in detail the front portion of the dart of this invention.
Figure 8:
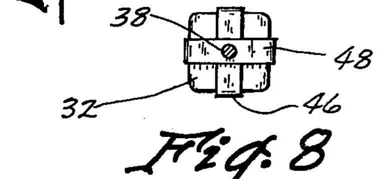
FIG. 8 is a view along line 8—8 of FIG. 7 showing the attachment of the release rubber bands to the power head sealing pin.

Rubber bands 46 and 48 are used to bias plunger 28 to a normally closed position. The rubber bands are loaded by piercing them through tubular needle 24 and moving them downwardly so that they preferably cross counterweight 42 as depicted in FIG. 6. The rubber bands are then extended rearwardly and crossed in like fashion as depicted in FIG. 8 over rearward plunger head 32. Pin portion 38 of power head sealing pin 36 is thereafter inserted through the rubber bands into the rearward portion of plunger 28. Rubber bands 40 and 42 are thus securely held in position on the innoculating dart by pin 38 at the rearward portion of the plunger and at the forward portion of the innoculating dart by tubular needle 24.

Figure 7:
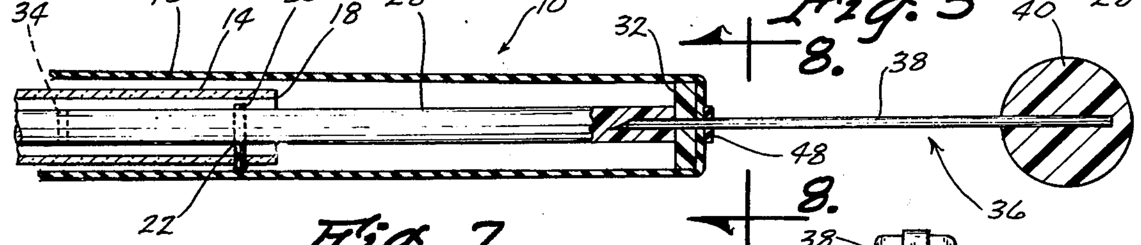
FIG. 7 is a sectional view, with certain parts broken away, of the rear portion of the dart in its loaded or cocked position.

To load the innoculating dart 10, plunger 28 is pulled rearwardly with tubular needle 24 inserted in the innoculating fluid. The fluid is drawn into syringe barrel 14 until the desired amount of fluid as specified by barrel markings 20 is indicated. As the desired fluid level, a break-away shear pin 50 is inserted through rear barrel end opening 22 and through one of the spaced apart apertures 34 in plunger 28. If desired, a shear pin 50 may be extended completely through both walls of cylindrical barrel 14; however, it has been found preferable in order to assure quick easy shearing action upon impact, that shear pin 40 be extended completely through plunger 28 and through only a single wall of barrel 14. After insertion of shear pin 50 through syringe barrel 14's alignment aperture 22, the plunger 28 is held in its cocked position as depicted in FIG. 7.

The dart 10 is thereafter inserted into blow gun 12 and sealing head 40 matingly fits within the interior diameter of blow gun 12 in order to provide a loose but effective air seal. The blow gun is thereafter lifted to the mouth, air expelled into the blow gun which impacts against sealing head 40 and causes dart 10 to be expelled out of the forward portion of the blow gun. Upon impact with an animal, the impact force causes easy break-away shear pin 50 to break and rubber bands 42 and 44 pull plunger 28 to its forward closed position, expelling the innoculating drug through tubular needle 24 into the target animal.

Certain constructional features of the innoculating dart are worthy of specific mention. The blow gun innoculating dart has been especially designed so that a conventional mechanical pencil lead may be conveniently used for break-away shear pin 50. It has been found preferable to utilize colored pencil leads which are of a clay base as those have been found to have the appropriate impact shear force. However, other leads may also be used besides clay based leads, such as china lead, conventional graphite lead, or the like. Where pencil leads as specified herein are utilized, it has been found convenient to provide as rubber bands 46 and 48 a pair of one-eighth inch by three inch gum rubber bands. Such rubber bands have been found to provide the correct amount of biasing means in order to assure that the innoculating dart will be conveniently expelled and that sufficient force will be provided to shear pin 50 upon impact, without having to worry about pin 50 being sheared prematurely.

Providing counterweight 42 having flattened side portions 44, has been found desirable for conveniently maintaining rubber bands 46 and 48 in position.

Sealing head 40 of power head sealing pin 36 is preferably a plastic bead with, as specified previously, the bead diameter corresponding to the inside diameter of blow gun 12. Plastic macrame beads have also been found to work equally well.

In actual use, the dart of this invention can be quickly loaded, conveniently shot, without any noise, accurately shot, and can therefore be used in crowded urban areas and the like. In addition, the dart is extremely inexpensive and can be provided along with a blow gun in kit form at a minimal cost for use by humane officers, zoo personnel, veterinary personnel, and others. Thus, as can be seen, the invention accomplishes at least all of its stated objects as specified.

What is claimed is:

1. An innoculating dart for blow guns, comprising
a hollow syringe barrel having forward and rearward ends,
and having near its rearward end, an alignment aperture, a tubular needle in communication with said syringe barrel
positioned at the forward end of said syringe barrel, and a plunger having front and back ends, reciprocally mounted
within the rearward end of said barrel, a power head sealer mounted on said dart, biasing means associated with said plunger to normally urge
said plunger to a closed forward position in said barrel, and
a plurality of spaced apart transverse openings extending through said plunger, for mating alignment with the alignment aperture of said syringe barrel, and
an easy break-away shear pin which may be extended through said alignment aperture of said syringe barrel and any one of said transverse opening at least partially across the rearward end of said syringe barrel to releasably hold said plunger in a cocked, rearward position.

2. The innoculating dart of claim 1 wherein said easy break-away shear pin is a clay based mechanical pencil lead material.

3. The innoculating dart of claim 1 wherein a counterweight is positioned over said tubular needle.

4. The innoculating dart of claim 1 wherein said biasing means are rubber bands.

5. The innoculating dart of claim 4, wherein said rubber bands are pierced through said tubular needle and extend rearwardly therefrom over the back end of said plunger.

6. The innoculating dart of claim 1 in combination with an innoculating dart blow gun having an interior bore, wherein said power head sealer is comprised of a forward extending pin portion and a sealing head mounted to said pin portion, said sealing head having a diameter generally equal to the interior bore diameter of said blow gun through which said dart is to be expelled.

* * * * *